United States Patent
Tomita

(10) Patent No.: US 11,191,703 B2
(45) Date of Patent: Dec. 7, 2021

(54) NON-STICKY BODY SURFACE PATCH

(71) Applicant: SHISEIDO COMPANY, LTD., Tokyo (JP)

(72) Inventor: Noriko Tomita, Kanagawa (JP)

(73) Assignee: SHISEIDO COMPANY, LTD., Tokyo (JP)

( * ) Notice: Subject to any disclaimer, the term of this patent is extended or adjusted under 35 U.S.C. 154(b) by 0 days.

(21) Appl. No.: 16/481,682

(22) PCT Filed: Jan. 30, 2018

(86) PCT No.: PCT/JP2018/002887
§ 371 (c)(1),
(2) Date: Jul. 29, 2019

(87) PCT Pub. No.: WO2018/143169
PCT Pub. Date: Aug. 9, 2018

(65) Prior Publication Data
US 2019/0374443 A1     Dec. 12, 2019

(30) Foreign Application Priority Data

Feb. 1, 2017   (JP) .............................. JP2017-016721

(51) Int. Cl.
*A61K 8/25* (2006.01)
*A61K 8/02* (2006.01)
*A61K 8/81* (2006.01)
*A61Q 19/00* (2006.01)

(52) U.S. Cl.
CPC .............. *A61K 8/0208* (2013.01); *A61K 8/25* (2013.01); *A61K 8/8111* (2013.01); *A61Q 19/00* (2013.01); *A61Q 19/001* (2013.01); *A61Q 19/007* (2013.01)

(58) Field of Classification Search
CPC ...................................................... A61K 8/25
See application file for complete search history.

(56) References Cited

U.S. PATENT DOCUMENTS

| | | | | |
|---|---|---|---|---|
| 4,943,462 A | * | 7/1990 | Komerska | A61K 8/0208 |
| | | | | 132/320 |
| 2012/0128966 A1 | * | 5/2012 | Ma | C09J 7/26 |
| | | | | 428/317.3 |
| 2014/0363488 A1 | | 12/2014 | Hansen et al. | |

FOREIGN PATENT DOCUMENTS

| | | | | |
|---|---|---|---|---|
| JP | 2007-284370 A | | 11/2007 | |
| JP | 5677303 B2 | | 2/2015 | |
| JP | 201566408 A | * | 4/2015 | |
| JP | 2015066408 A | | 4/2015 | |
| JP | 2015110294 A | | 6/2015 | |
| JP | 2015131004 A | | 7/2015 | |
| JP | 2015168626 A | | 9/2015 | |
| JP | 2016-123866 A | | 7/2016 | |
| WO | 2010086901 A1 | | 8/2010 | |
| WO | 2015072021 A1 | | 5/2015 | |
| WO | 2016179610 A1 | | 11/2016 | |

OTHER PUBLICATIONS

ShinEtsu (Comprehensive Product Guide, 2014). (Year: 2014).*
International Search Report dated May 15, 2018 filed in PCT/JP2018/002887; partial translation.
Written Opinion of the International Searching Authority, dated May 15, 2018 filed in PCT/JP2018/002887; partial translation.
Extended European Search Report (EESR) dated Dec. 3, 2020 issued in the corresponding European Patent Application No. 18748047.0.

* cited by examiner

*Primary Examiner* — Benjamin J Packard
(74) *Attorney, Agent, or Firm* — Rankin, Hill & Clark LLP

(57) ABSTRACT

A non-sticky body surface patch is provided, which is attachable on a body surface to add a look of fullness to the body surface, exhibits excellent followability to skin deformation, and imposes little burden on body surfaces and thus is widely applicable to body surfaces. The non-sticky body surface patch includes a silicone rubber having a thickness in the range from 50 to 600 μm, wherein the silicone rubber consists of a silicone rubber composition having a rubber hardness of 20 or less measured with a Type A durometer as defined in JIS K6249 standard.

14 Claims, No Drawings

NON-STICKY BODY SURFACE PATCH

CROSS-REFERENCE TO RELATED APPLICATIONS

This application is a National Phase Entry of PCT International Application No. PCT/JP2018/002887 filed on Jan. 30, 2018, which claims priority under 35 U.S.C § 119(a) to Japanese Patent Application No. 2017-016721 filed on Feb. 1, 2017. Each of the above applications is hereby expressly incorporated by reference, in its entirety, into the present application.

TECHNICAL FIELD

The present disclosure pertains to a non-sticky body surface patch.

BACKGROUND ART

One phenomenon of aging of the skin along with increase of age is increase of wrinkles. In view of beauty care, or the like, in particular for females, prevention and improvement of wrinkles are of very high interest. In particular, the lips are one of the body sites where changes of the shape, among skin troubles including aging, is highly noticeable. Troubles regarding the lips may include roughness and dullness of the lip skin, as well as increase of wrinkles on the lips and decrease of fullness with aging.

Japanese Unexamined Patent Publication No. 2015-168626 (hereinafter, Patent Literature 1) teaches a patch for lips comprising a support layer, an adhesive layer, and a separator layer which are laminated one on the other. This patch for lips is attached to the surface of the lips to add the lips with color and gloss without using a lip cosmetic, and also provides other effects, such as protection, to the lips. WO 2015/072021 (hereinafter, Patent Literature 21 teaches a patch for covering a lip cosmetic to improve durability of the makeup effects of the lip cosmetic, such as a lipstick, and to prevent color migration and color bleeding of the lip cosmetic.

Japanese Patent No. 5677303 (hereinafter, Patent Literature 3) teaches a laminate structure for makeup which comprises a substrate made of a flexible material, such as polyurethane, an image forming layer with a color image for modifying the skin printed thereon, a hot melt adhesive layer, and a water-permeable protection layer. This laminate structure for makeup is adhered to the skin to conceal a defect on the skin.

SUMMARY

The patches for lips taught in Patent Literature 1 and 2, however, are not directed to add a look of fullness to the lips, and have such problems as burden imposed on the lips by the adhesive layer, significant uncomfortable feeling, and poor followability to skin deformation. Also, the laminate structure for makeup taught in Patent Literature 3 is not directed to add a look of fullness to the lips. The laminate structure of Patent Literature 3 is used to compensate for a defect on the skin with the image forming layer having a color image for modifying the skin printed thereon, and therefore requires to prepare the image forming layer correspondingly to the body site to which the laminate structure is attached. Further, in view of the burden imposed on the skin, it is difficult to apply the laminate structure of Patent Literature 3 to delicate body sites, such as the face and the lips.

In view of the above-described circumstances, the present disclosure is directed to providing a non-sticky body surface patch which is attachable on a body surface to add a look of fullness to the body surface, exhibits excellent followability to skin deformation, and imposes little burden on body surfaces and thus is widely applicable to body surfaces.

A non-sticky body surface patch of the disclosure comprises a silicone rubber having a thickness in the range from 50 to 600 µm, wherein the silicone rubber consists of a silicone rubber composition having a rubber hardness of 20 or less measured with a Type A durometer as defined in JIS K6249 standard.

The term "body surface", as used herein, refers to the skin of any site of the body (such as the face, hands, legs, chest, lower stomach, back, or the like), and the skin includes lips, nails, which are formed by altered and hardened cuticle in the epidermis of the skin, and even scarred skin surfaces.

It is more preferred that the rubber hardness be 10 or less.

The thickness is preferably in the range from 50 to 400 µm, more preferably in the range from 50 to 300 µm, and particularly preferably greater than or equal to 50 µm and less than or equal to 200 µm.

The non-sticky body surface patch of the disclosure may be a patch for lips.

The non-sticky body surface patch of the disclosure may be a patch for skin around eyes, and in this case, the thickness is preferably greater than or equal to 50 µm and less than or equal to 500 µm.

The non-sticky body surface patch of the disclosure may comprise a release sheet.

A makeup kit of the disclosure comprises the above-described non-sticky body surface patch of the disclosure.

It is preferred that the makeup kit comprise an adhesion agent.

It is preferred that the adhesion agent comprise polybutene or polyisobutene.

It is preferred that the adhesion agent comprise a moisturizing component.

Advantageous Effects of Disclosure

The non-sticky body surface patch of the disclosure, which comprises a silicone rubber having a thickness in the range from 50 to 600 µm, wherein the silicone rubber consists of a silicone rubber composition having a rubber hardness of 20 or less measured with a Type A durometer as defined in JIS K6249 standard, is attachable on a body surface to add a look of fullness to the body surface, exhibits excellent followability to skin deformation, and imposes little burden on body surfaces and thus is widely applicable to body surfaces.

DESCRIPTION OF EMBODIMENTS

Now, a non-sticky body surface patch of the disclosure will be described in detail.

The non-sticky body surface patch of the disclosure includes a silicone rubber having a thickness in the range from 50 to 600 µm, wherein the silicone rubber consists of a silicone rubber composition having a rubber hardness of 20 or less measured with a Type A durometer as defined in JIS K6249 standard.

The non-sticky body surface patch of the disclosure is made of a silicone rubber having a thickness in the range from 50 to 600 µm. The thickness may be changed, as appropriate, from the above-defined range depending on movement of the body site where the patch is applied and the use thereof. For example, in the case where the non-sticky body surface patch is used to add a look of fullness to a body site, such as the lips, which moves frequently, the thickness is preferably in the range from 50 to 400 μm, more preferably in the range from 50 to 300 μm, and particularly preferably greater than or equal to 50 μm and less than or equal to 200 μm. In the case where the non-sticky body surface patch is attached in the vicinity of a body site, such as the nose, which moves but not as frequent as the lips, to add a look of fullness to the nose, or attached to the nose bridge to make it look higher, the thickness is preferably greater than or equal to 50 μm and less than or equal to 500 μm. In the case where the non-sticky body surface patch is attached below the eyes to add a look of fullness to the eye bags (immediately below the eyes), or to make those who do not have eye bags look as if they have eye bags, the thickness is preferably adjusted depending on the purpose within the range greater than or equal to 50 μm and less than or equal to 500 μm. Further, in the case where the non-sticky body surface patch is used like a nail seal or a nail gel to add a thickness to the nails to make unevenness, flatness, or vertical lines of the nails less noticeable, the thickness is preferably greater than or equal to 50 μm and less than or equal to 600 μm.

The "thickness" of the non-sticky body surface patch, as used herein, is an average value of five measurements performed at arbitrary portions of the non-sticky body surface patch using a precision thickness meter (PEACOCK dial thickness gauge 0.01 mm type, available from Ozaki Mfg. Co., Ltd).

In the case where the non-sticky body surface patch of the disclosure is applied to the lips, for example, the thickness of the marginal area of the non-sticky body surface patch may be decreased depending on the body site to which the patch is applied. It should be noted that the thickness in this case is an average value of measurements performed at the thickest portion of the non-sticky body surface patch in the same manner as described above.

The non-sticky body surface patch may be provided with slit-like cut lines in the surface thereof attached to the body site, such as the lips or the eyes, depending on the body site to which the patch is applied, to facilitate the patch to conform to wrinkles on or movements of the body site.

The silicone rubber is obtained by curing the silicone rubber composition. The silicone rubber consists of a silicone rubber composition having a rubber hardness of 20 or less measured with a Type A durometer as defined in JIS K6249 standard. The silicone rubber composition preferably has a rubber hardness of 10 or less, and more preferably 5 or less. A rubber hardness of 20 or less of the silicone rubber composition allows the patch to add a look of fullness to the body surface to which the patch is attached, and exhibit good followability to skin deformation and excellent durability of the effects. Thus, when the patch is applied to a body surface, in particular, the lips, which is frequently moved, the patch causes little uncomfortable feeling, and endures the movement of the lips even when the user is having a snack. Since the patch is not sticky, it imposes little burden on body surfaces and thus is applicable even to a scarred skin. Further, since the patch can add a look of fullness to the skin surface to which it is applied, the patch is also applicable to concealing a scar. It should be noted that the silicone rubber composition preferably has a rubber hardness of 3 or more. A rubber hardness of 3 or more of the silicone rubber composition allows keeping the strength of the silicone rubber.

The silicone rubber composition may be any type of curable silicone rubber composition; however, those obtained from an addition (hydrocyrilizing) reaction-curable silicone rubber composition or an organic peroxide-curable silicone rubber composition are preferred since they can be molded in a short tune by heating. The addition reaction-curable silicone rubber composition may be any of known compositions, and one containing: an alkenyl-containing organopolysiloxane having two or more alkenyl groups, such as vinyl groups, in a molecule; an organohydrogen polysiloxane having two or more, preferably three or more SiH groups (usually in such an amount that the molar ratio of the SiH groups to the alkenyl groups is 0.5 to 4); and a platinum family metal addition reaction catalyst, such as platinum or a platinum compound (usually in an amount of 1 to 1000 ppm relative to the alkenyl-containing organopolysiloxane). The organic peroxide curable silicone rubber composition may be any of known compositions, and is preferably an organopolysiloxane having two or more alkenyl groups in a molecule with an organic peroxide, which serves as a curing agent, added thereto in an amount effective to achieve curing (usually in an amount of 1 to 10 parts by mass relative to 100 parts by mass of the organopolysiloxane).

As the silicone rubber composition, commercially available products can be used. Examples of the commercially available products of the addition reaction-curable silicone rubber composition may include those of LIMS (liquid silicone rubber injection molding system), such as KE-1950-10A/B, KE-1950-20A/B, KE-2004-3A/B, and KE-2004-5A/B, available from Shin-Etsu Chemical Co., Ltd. The non-sticky body surface patch of the disclosure is a silicone rubber having a thickness in the range from 50 to 500 μm obtained by curing the above-described silicone rubber composition.

The non-sticky body surface patch of the disclosure has a hardness of 51 or less measured with the ASKER Durometer Type C1L as defined in JIS K7312 standard in a state where the patches are stacked such that the total thickness is 12 mm. Specifically, in a case where the silicone rubber composition having a rubber hardness of 20 measured with the Type A durometer as defined in JIS K6249 standard is cured to form sheets each having a thickness of 100 μm, and the sheets are stacked such that the total thickness is 12 mm, the stack has a hardness of 51 measured with the ASKER Durometer Type C1L as defined in JIS K7312 standard. Further, in a case where the silicone rubber composition having a rubber hardness of 5 measured with the Type A durometer as defined in JIS K6249 standard is cured to form sheets each having a thickness of 100 μm, and the sheets are stacked such that the total thickness is 12 mm, the stack has a hardness of 31 measured with the ASKER Durometer Type C1L as defined in JIS K7312 standard.

The non-sticky body surface patch (sheet) of the disclosure can be produced using a known production method. Specific examples of the production method may include: directly obtaining the sheet from the silicone rubber composition using compression molding, injection molding, or the like; or fainting the sheet on a metal substrate, a resin substrate, or a resin film using insert molding. In the case where insert molding is used, a release sheet, which will be described below, may be used such that the non-sticky body surface sheet is formed on the release sheet.

In view of handing, the non-sticky body surface patch of the disclosure may include the release sheet. Since the non-sticky body surface patch of the disclosure is very thin, the patch can adhere to the release sheet due to electro-static effect.

The release sheet is not particularly limited; however, examples thereof may include polyethylene, polypropylene, polyethylene terephthalate, or the like, in view of handling.

Since the non-sticky body surface patch of the disclosure is not sticky, an adhesion agent is applied to a body surface before the patch is attached to the body surface, and the non-sticky body surface patch is attached to the area of the body surface where the adhesion agent is applied. It is preferred that the adhesion agent impose little burden on the skin, and preferred examples of the adhesion agent may include those containing polybutene or polyisobutene. Polybutene or polyisobutene having an average molecular weight of 1000 or more is preferred.

The adhesion agent may contain a moisturizing component. As the moisturizing component, those commonly used in cosmetics can be applied. Examples thereof may include polyethylene glycol, propylene glycol, glycerin, 1,3-butylene glycol, dipropylene glycol, xylitol, sorbitol, maltitol, chondroitin sulfate, hyaluronic acid, mucoitinsulfuric acid, colanic acid, atelocollagen, sodium lactate, pyrrolidine carboxylic acid, short chain soluble collagen, and the like.

The moisturizing component is preferably added in a ratio of 0.01 to 10 mass % relative to 100 mass % of the adhesion agent.

The non-sticky body surface patch of the disclosure may be provided in combination with the adhesion agent as a makeup kit.

thereto. After three hours, the panelists had a meal, and then visually checked the state of attachment immediately after the meal and evaluated the samples according to the criteria shown below.

Look of Fullness
A: Wrinkles were less noticeable and a look of fullness was added when compared to the naked lips.
B: Unevenness was somewhat noticeable, but a look of fullness was added when compared to the naked lips.
C: Unevenness was noticeable and a look of fullness was not added.

Naturalness of Appearance
A: The boundary between the patch and the skin was not noticeable and the appearance was natural.
B: The boundary between the patch and the skin was somewhat noticeable, but the appearance was natural when seen from a distance.
C: The boundary between the patch and the skin was noticeable and the appearance was unnatural.

Followability to Skin Deformation
AA: No partial separation of the patch from the skin was observed.
A: With the lips puckered, partial separation of less than ⅓ of the entire patch from the skin was observed.
B: With the lips puckered, partial separation of around ⅓ of the entire patch from the skin was observed.
C: With the lips puckered, partial separation of ½ or more of the entire patch from the skin was observed.

Durability
AA: No peeling was observed.
A: Peeling of less than ⅓ of the entire patch was observed.
B: Peeling of around ⅓ of the entire patch was observed.
C: Peeling of ½ or more of the entire patch was observed.

The results of the evaluation are shown in Table 1.

TABLE 1

|  | Test Example 1 | Test Example 2 | Test Example 3 | Test Example 4 | Test Example 5 | Test Example 6 |
| --- | --- | --- | --- | --- | --- | --- |
| Thickness (μm) | 50 | 100 | 200 | 300 | 400 | 500 |
| Rubber Hardness | 5 | 5 | 5 | 5 | 5 | 5 |
| Fullness | A | A | A | A | A | B |
| Naturalness | A | A | A | A | B | C |
| Followability | AA | AA | A | B | B | C |
| Durability | AA | AA | AA | A | B | B |

EXAMPLES

Now, more detailed description of the non-sticky body surface patch of the disclosure is given with reference to Test Examples and Examples.

Test Examples 1 to 6

A silicone rubber composition, LIMS, KE 2004-5A/F3 (having a rubber hardness of 5), available from Shin-Etsu Chemical Co., Ltd., was used to prepare lip-shaped samples (an oval shape having a width of 35 mm and a height of 7 mm, and a uniform thickness over the entire area) having thicknesses of 50 μm, 100 μm, 200 μm, 300 μm, 400 μm, and 500 μm, respectively. In the test, first, female panelists in their forties and fifties applied an adhesion agent, which containined polybutene (having a molecular weight of 2650) and polyisobutene (having a molecular weight of 55000), to their lips, and then attached each of the prepared samples As shown in Table 1, the non-sticky body surface patches of Test Examples 1 to 5 added a look of fullness to the lips, provided natural appearance, and had good followability to skin deformation and good durability.

Test Examples 7 to 12

A silicone rubber composition, LIMS, KE-2004-10A/B (having a rubber hardness of 10), available from Shin-Etsu Chemical Co., Ltd., was used to prepare lip-shaped samples (an oval shape having a width of 35 mm and a height of 7 mm) having thicknesses of 50 μm, 100 μm, 200 μm, 300 μm, 400 μm, and 500 μm, respectively, and the samples were evaluated in the same manner as described above with respect to Test Examples 1 to 6.

The results of the evaluation are shown in Table 2.

TABLE 2

|  | Test Example 7 | Test Example 8 | Test Example 9 | Test Example 10 | Test Example 11 | Test Example 12 |
| --- | --- | --- | --- | --- | --- | --- |
| Thickness (μm) | 50 | 100 | 200 | 300 | 400 | 500 |
| Rubber Hardness | 10 | 10 | 10 | 10 | 10 | 10 |
| Fullness | A | A | A | A | A | B |
| Naturalness | A | A | B | B | B | C |
| Followability | AA | AA | B | B | C | C |
| Durability | AA | AA | A | B | B | C |

As shown in Table 2, the non-sticky body surface patches of Test Examples 7 to 10 added a look of fullness to the lips, provided natural appearance, and had good followability to skin deformation and good durability.

Test Examples 13 to 18

A silicone rubber composition, KE-2004-20A/B (having a rubber hardness of 20), available from Shin-Etsu Chemical Co., Ltd., LIMS, was used to prepare lip-shaped samples (an oval shape having a width of 35 mm and a height of 7 mm) having thicknesses of 50 μm, 100 μm, 200 μm, 300 μm, 400 μm, and 500 μm, respectively, and the samples were evaluated in the same manner as described above with respect to Test Examples 1 to 6.

The results of the evaluation are shown in Table 3.

TABLE 3

|  | Test Example 13 | Test Example 14 | Test Example 15 | Test Example 16 | Test Example 17 | Test Example 18 |
| --- | --- | --- | --- | --- | --- | --- |
| Thickness (μm) | 50 | 100 | 200 | 300 | 400 | 500 |
| Rubber Hardness | 20 | 20 | 20 | 20 | 20 | 20 |
| Fullness | A | B | B | B | B | C |
| Naturalness | A | B | B | B | B | C |
| Followability | A | B | B | B | C | C |
| Durability | AA | AA | A | B | B | C |

As shown in Table 3, the non-sticky body surface patches of Test Examples 13 to 16 added a look of fullness to the lips, provided natural appearance, and had good followability to skin deformation and good durability.

Examples 1 to 5, Comparative Example 1

A silicone rubber composition, LIMS, KE-2004-3A/B (having a rubber hardness of 3), available from Shin-Etsu Chemical Co., Ltd., was used to prepare eye bag-shaped samples (an oval shape having a width of 15 mm and a height of 2 mm, and a uniform thickness over the entire area) having thicknesses of 50 μm, 100 μm, 200 μm, 300 μm, 500 μm, and 650 μm, respectively. In the test, first, female panelists in their forties and fifties applied an adhesion agent, which contatinined polybutene (having a molecular weight of 2650) and polyisobutene (having a molecular weight of 55000), to their eye bags (or positions corresponding to eye bags for those who did not have eye bags), and then attached each of the prepared samples thereto. After eight hours of their daily living activities, the panelists performed visual check and evaluation of the samples according to the criteria shown below.

Look of Fullness

A: No unevenness was noticeable and a look of fullness was added to the areas below the eyes.

B: Unevenness was somewhat noticeable, but a look of fullness was added to the areas below the eyes.

C: Unevenness was noticeable and no look of fullness was added.

Naturalness of Appearance

A: The boundary between the patch and the skin was not noticeable and the appearance was natural.

B: The boundary between the patch and the skin was somewhat noticeable, but the appearance was natural when seen from a distance.

C: The boundary between the patch and the skin was noticeable and the appearance was unnatural.

Followability to Skin Deformation

AA: No partial separation of the patch from the skin was observed.

A: When smiling, partial separation of less than ⅓ of the entire patch from the skin was observed.

B: When smiling, partial separation of around ⅓ of the entire patch from the skin was observed.

C: When smiling, partial separation of ½ or more of the entire patch from the skin was observed.

Durability

AA: No peeling was observed.

A: Peeling of less than ⅓ of the entire patch was observed.

B: Peeling of around ⅓ of the entire patch was observed.

C: Peeling of ½ or more of the entire patch was observed.

The results of the evaluation are shown in Table 4.

TABLE 4

|  | Example 1 | Example 2 | Example 3 | Example 4 | Example 5 | Comp. Example 1 |
|---|---|---|---|---|---|---|
| Thickness (μm) | 50 | 100 | 200 | 300 | 500 | 650 |
| Rubber Hardness | 3 | 3 | 3 | 3 | 3 | 3 |
| Fullness | A | A | A | A | A | B |
| Naturalness | A | A | A | A | B | C |
| Followability | AA | AA | A | A | A | B |
| Durability | AA | AA | AA | A | A | C |

As shown in Table 4, the non-sticky body surface patch of the disclosure added a look of fullness to eye bags, provided natural appearance, and had good followability to skin deformation and good durability.

Examples 6 to 10, Comparative Example 2

A silicone rubber composition, LIMS, KE-2004-5A/B (having a rubber hardness of 5), available from Shin-Etsu Chemical Co., Ltd., was used to prepare eye bag-shaped samples (an oval shape having a width of 15 mm and a height of 2 mm, and a uniform thickness over the entire area) having thicknesses of 50 μm, 100 μm, 200 μm, 300 μm, 500 μm, and 650 μm, respectively, and the samples were evaluated in the same manner as described above with respect to Examples 1 to 5 and Comparative Example 1.

The results of the evaluation are shown in Table 5.

TABLE 5

|  | Example 6 | Example 7 | Example 8 | Example 9 | Example 10 | Comp. Example 2 |
|---|---|---|---|---|---|---|
| Thickness (μm) | 50 | 100 | 200 | 300 | 500 | 650 |
| Rubber Hardness | 5 | 5 | 5 | 5 | 5 | 5 |
| Fullness | A | A | A | A | A | B |
| Naturalness | A | A | A | A | B | C |
| Followability | AA | AA | A | A | A | C |
| Durability | AA | AA | AA | A | A | C |

As shown in Table 5, the non-sticky body surface patch of the disclosure added a look of fullness to eye bags, provided natural appearance, and had good followability to skin deformation and good durability.

Examples 11 to 15, Comparative Example 3

A silicone rubber composition, LIMS, KE-1950-10A/B (having a rubber hardness of 10), available from Shin-Etsu Chemical Co., Ltd., was used to prepare eye bag-shaped samples (an oval shape having a width of 15 mm and a height of 2 mm, and a uniform thickness over the entire area) having thicknesses of 50 μm, 100 μm, 200 μm, 300 μm, 500 μm, and 650 μm, respectively, and the samples were evaluated in the same manner as described above with respect to Examples 1 to 5 and Comparative Example 1.

The results of the evaluation are shown in Table 6.

TABLE 6

|  | Example 11 | Example 12 | Example 13 | Example 14 | Example 15 | Comp. Example 3 |
|---|---|---|---|---|---|---|
| Thickness (μm) | 50 | 100 | 200 | 300 | 500 | 650 |
| Rubber Hardness | 10 | 10 | 10 | 10 | 10 | 10 |
| Fullness | A | A | A | A | A | B |
| Naturalness | A | A | A | B | B | C |
| Followability | AA | AA | A | B | B | C |
| Durability | AA | AA | A | A | B | C |

As shown in Table 6, the non-sticky body surface patch of the disclosure added a look of fellness to eye bags, provided natural appearance, and had good followability to skin deformation and good durability.

Examples 16 to 20, Comparative Example 4

A silicone rubber composition available from Shin-Etsu Chemical Co., Ltd., LIMS, KE-1950-20A/B (having a rubber hardness of 20) was used to prepare eye bags shaped samples (an oval shape having a width of 15 mm and a height of 2 mm, and a uniform thickness over the entire area) having thicknesses of 50 μm, 100 μm, 200 μm, 300 μm, 500 μm, and 650 μm, respectively, and the samples were evaluated in the same manner as described above with respect to Examples 1 to 5 and Comparative Example 1.

The results of the evaluation are shown in Table 7.

TABLE 7

|  | Example 16 | Example 17 | Example 18 | Example 19 | Example 20 | Comp. Example 4 |
| --- | --- | --- | --- | --- | --- | --- |
| Thickness (μm) | 50 | 100 | 200 | 300 | 500 | 650 |
| Rubber Hardness | 20 | 20 | 20 | 20 | 20 | 20 |
| Fullness | A | A | A | A | B | C |
| Naturalness | A | A | A | B | B | C |
| Followability | A | B | B | B | B | C |
| Durability | AA | AA | A | A | B | C |

As shown in Table 7, the non-sticky body surface patch of the disclosure added a look of fullness to eye bags, provided natural appearance, and had good followability to skin deformation and good durability.

While the above Examples are described with respect to the cases where the non-sticky body surface patch of the disclosure is applied to lips or eye bags, the body sites to which the non-sticky body surface patch of the disclosure is applicable are not limited to lips and eye bags, and the patch is widely applicable to body surfaces, such as the face, hands, legs, and even scarred body sites.

The invention claimed is:

1. A non-sticky body surface patch comprising a silicone rubber having a thickness in the range from 50 to 300 μm, wherein the silicone rubber consists of a silicone rubber composition having a rubber hardness of 20 or less measured with a Type A durometer as defined in JIS K6249 standard and containing an alkenyl-containing organopolysiloxane having two or more alkenyl groups in a molecule and an organohydrogen polysiloxane having two or more SiH groups.

2. The non-sticky body surface patch as claimed in claim 1, wherein the rubber hardness is 10 or less.

3. The non-sticky body surface patch as claimed in claim 1, wherein the patch is a patch for lips.

4. The non-sticky body surface patch as claimed in claim 1, wherein the patch is a patch for skin around eyes.

5. The non-sticky body surface patch as claimed in claim 1, comprising a release sheet.

6. A makeup kit comprising the non-sticky body surface patch as claimed in claim 1.

7. The makeup kit as claimed in claim 6, further comprising an adhesion agent.

8. The makeup kit as claimed in claim 7, wherein the adhesion agent comprises polybutene and/or polyisobutene.

9. The makeup kit as claimed in claim 7, wherein the adhesion agent comprises a moisturizing component.

10. The non-sticky body surface patch as claimed in claim 2, wherein the patch is a patch for lips.

11. The non-sticky body surface patch as claimed in claim 2, wherein the patch is a patch for skin around eyes.

12. The non-sticky body surface patch as claimed in claim 2, comprising a release sheet.

13. The non-sticky body surface patch as claimed in claim 4, comprising a release sheet.

14. The makeup kit as claimed in claim 8, wherein the adhesion agent comprises a moisturizing component.

* * * * *